United States Patent
Kallergi et al.

(10) Patent No.: US 6,630,937 B2
(45) Date of Patent: Oct. 7, 2003

(54) WORKSTATION INTERFACE FOR USE IN DIGITAL MAMMOGRAPHY AND ASSOCIATED METHODS

(75) Inventors: Maria Kallergi, Tampa, FL (US); Laurence P. Clarke, Darnstown, MD (US); Himanshu J. Gohel, Santa Ana, CA (US); Michal Vossberg, Berlin (DE)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 10/081,135

(22) Filed: Feb. 22, 2002

(65) Prior Publication Data

US 2003/0026503 A1 Feb. 6, 2003

Related U.S. Application Data

(63) Continuation of application No. 09/255,131, filed on Feb. 19, 1999, now abandoned, and a continuation-in-part of application No. 08/960,815, filed on Oct. 30, 1997, now Pat. No. 5,987,094.
(60) Provisional application No. 60/075,443, filed on Feb. 20, 1998.

(51) Int. Cl.$^7$ ................................................. G09G 5/00
(52) U.S. Cl. .................. 345/619; 345/618; 345/589; 345/690; 345/698; 345/1.1; 345/204; 345/1.2; 382/128; 382/131; 382/132; 382/274; 382/276
(58) Field of Search ........................... 345/418–426, 345/428, 581, 588, 589, 595, 603, 618, 619, 621, 633, 632–635, 660, 156, 1.2, 173–175, 176, 1.1, 112–116, 118, 121, 132, 204–207, 690, 698, 214, 10–12; 382/128, 129, 131, 132, 254, 130, 274–276, 284; 600/425, 300; 705/2, 3; 378/62; 40/361

(56) References Cited

U.S. PATENT DOCUMENTS

| | | | | |
|---|---|---|---|---|
| 4,982,345 A | * | 1/1991 | Callahan et al. | 358/518 |
| 5,172,103 A | * | 12/1992 | Kita | 340/731 |
| 5,659,362 A | * | 8/1997 | Kovac | 348/384 |
| 5,854,851 A | * | 12/1998 | Bamberger et al. | 382/132 |
| 5,872,859 A | * | 2/1999 | Gur | 382/128 |
| 5,896,169 A | * | 4/1999 | Boelart | 348/181 |
| 5,917,929 A | * | 6/1999 | Marshall et al. | 382/128 |
| 5,946,407 A | * | 8/1999 | Bamberger et al. | 382/132 |
| 5,970,164 A | * | 10/1999 | Bamberger et al. | 382/128 |
| 5,987,094 A | * | 11/1999 | Clarke et al. | 378/62 |
| 6,006,191 A | * | 12/1999 | DiRienzo | 705/2 |
| RE36,653 E | * | 4/2000 | Heckel et al. | 345/340 |
| 6,058,322 A | * | 5/2000 | Nishikawa et al. | 600/408 |
| 6,178,224 B1 | * | 1/2001 | Polichar et al. | 378/98.2 |
| 6,243,095 B1 | * | 6/2001 | Shile et al. | 345/437 |
| 6,266,435 B1 | * | 7/2001 | Wang | 382/132 |
| 6,424,332 B1 | * | 7/2002 | Powell | 345/156 |
| 6,434,261 B1 | * | 8/2002 | Zhang et al. | 382/132 |

FOREIGN PATENT DOCUMENTS

| | | | |
|---|---|---|---|
| WO | WO 99/05503 | * | 2/1999 |
| WO | WO 00/51484 | * | 9/2000 |

* cited by examiner

*Primary Examiner*—Matthew C. Bella
*Assistant Examiner*—Wesner Sajous
(74) *Attorney, Agent, or Firm*—Anton J. Hopen; Smith & Hopen, P.A.

(57) ABSTRACT

A workstation-user interface for evaluating computer assisted diagnosis (CAD) methods for digital mammography is disclosed. Implementation of such an interface enables multiple, large-size images to be handled at high speeds. Furthermore, controls such as contrast, pan, and zoom, and tools such as reporting forms, case information, and analysis of results are included. The software and hardware used to develop such a workstation and interface were based on Sun platforms and the Unix operating system. The software is user friendly, and comparable to standard mammography film reading in terms of display layout and speed. The software, as designed, will work on entry-level workstations as well as high-end workstations with specialized hardware, thus being usable in an educational, training, or clinical environment for annotation purposes using CAD techniques as well as primary diagnosis.

17 Claims, 12 Drawing Sheets

Mammography Interpretation and ROC Analysis (MIRA)
Mammography Report

Please sign in!   Date: 06-Feb-1998   case 1 / case 2 / case 3

Method:  ✓Standard     ✓Digital   ✓Digital+CAD
Overall Breast Composition:   ✓1  ✓2  ✓3  ✓4
Assessment Category:   1: Negative (N)
Finding:
✓Calcifications Character:   C Coarse / D Dystrophic / E Eggshell or Rim Distribution:   ? Select Number:   ? Select ⌃Mass Shape:   ? Select Margin:   O Circumscribed / M Microlobulated / U Obscured / I Indistinct Density:   ? Select

Location:

⌃Clockface:   ?

OR

✓Region:   ? Select

Side:   ? Select

Depth:   ? Select

Additional Comments:

[ Record data ] [ Record and go to next case ]
[ Registration ] [ Evaluation ] [ Quit ]

FIG. 12

WORKSTATION INTERFACE FOR USE IN DIGITAL MAMMOGRAPHY AND ASSOCIATED METHODS

CROSS-REFERENCE TO RELATED APPLICATION

This application is a continuation of and claims priority to U.S. application Ser. No. 09/255,131, filed Feb. 19, 1999 now abandoned, for Workstation Interface for Use in Digital Mammography and Associated Methods, which claims priority to U.S. provisional application Serial No. 60/075,443, filed Feb. 20, 1998, for "Workstation Interface for Use in Digital Mammography," and also is a continuation-in-part of U.S. Pat. No. 5,987,094, issued Nov. 16, 1999, Ser. No. 08/960,815, filed Oct. 30, 1997, for Computer-Assisted Method and Apparatus for the Detection of Lung Nodules, all of which are commonly owned with the present invention and which are incorporated herein by reference.

GOVERNMENT SUPPORT

The present invention was supported in part by a grant from Navy Medical Research and Development Command, U.S.U.H.S. MDA905-95-Z-0057.

FIELD OF THE INVENTION

The present invention relates to a workstation system and method for use with digitized medical imagery, particularly digitized mammograms, and, more particularly, to an interface system and method for providing a desired display form of the mammogram to a user.

BACKGROUND OF THE INVENTION

The imminent arrival of digital mammography brings with it a set of issues that must be resolved in order to make the technology easy to adapt to and therefore successful. New techniques must be developed to present the information to the radiologists effectively.[1-5] Moreover, any software written to assist diagnosis in digital mammography must be evaluated by radiologists before it can be deemed useful. Evaluation is usually done with receiver operating characteristic (ROC) experiments the design of which should consider and find remedies for possible reading biases.[6] Differences between monitor and viewbox reading of mammograms can introduce significant biases in an ROC study.

A review of the existing literature on display workstations indicates that the problem of displaying full digital mammograms for primary diagnosis is a continuing issue.[2] Commercial systems exist for several modalities that generate digital data including magnetic resonance imaging (MRI), computed tomography (CT), chest radiography, ultrasound, and nuclear medicine.[7] Current commercial workstations for digital mammography are used in stereotactic biopsy systems[8] or for CAD reporting on low-resolution images, while primary diagnosis is done from original films.[5] Hence, applications involving full, high-resolution digital mammogram review have had to resort to in-house development of the required display system.[3]

SUMMARY OF THE PRESENT INVENTION

It is thus an object of the present invention to provide a workstation interface for such applications that is designed in a way that is not technically intrusive.

It is another object to provide such a workstation interface that is comparable to the existing standard reading procedure.

It is a further object to provide such a workstation interface that provides all the advantages of currently available technology.

It is an additional object to develop a workstation interface for evaluating CAD methods for digital mammography in ROC experiments.

Another object is to provide software that is as natural and intuitive to use by radiologists as possible.

A further object is to provide such software that is open and flexible to permit easy changes and/or additions and allow usage not only as a clinical tool, but also as an educational or training tool.

These and other objects of the present invention are achieved by the present invention, a system and method for providing an interface between a medical image and a user. The system comprises means for establishing electronic communication with a processor for receiving a stored digitized medical image comprising data representative of a plurality of greyscale values. Further the system includes means for communicating with a display means, such as a monitor. Software means that are loadable into the processor comprise means for receiving a signal from a user-operable device and means controllable by a signal from the user-operable device for transforming the image into a plurality of varying-resolution forms, each form having a different set of greyscale values. In addition, the software means comprises means for displaying the forms on the display means, each form displayed within a different sector of the display means.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIGS. 4–13 illustrate a series of digitized mammogram displays produced by the principles of the present invention, in various states of illumination, and also how various features of the present invention are displayed and can be used by a radiologist in examining a digitized mammogram produced by the system of the present invention.

FIG. 4 illustrates a "regular" mammogram image.

FIG. 5 illustrates greyscale adjustment on a single image.

FIG. 6 illustrates a full view "popup" of one image.

FIG. 7 illustrates the use of a measuring square on an image.

FIG. 8 illustrates the use of a measuring ruler on an image.

FIG. 9 illustrates a CAD window on the left-hand side, prior to overlaying a CAD image.

FIG. 10 illustrates a CAD window on the left-hand side, after overlaying a CAD image.

FIG. 11 illustrates an exemplary patient/case information window.

FIG. 12 illustrates an exemplary reporting window.

FIG. 13 illustrates a preview image supplied to the user prior to viewing the detailed views.

DETAILED DESCRIPTION OF THE PREFERRED EMBODIMENTS

Introduction

The design, implementation, and evaluation of a workstation for digital mammography will be described in the following sections. The hardware and software sections discuss the technology used for the implementation of the present invention in a way that would provide a user-friendly interface, a fast (near-real-time) interactive response, and flexibility in design and use, at what is believed to be a reasonably low cost. The design and implementation section details the design choices and implementation of the present invention. It is to be understood by one of skill in the art that the hardware detailed herein is not intended to form a limitation on the invention, and that equivalent devices may be substituted therefor. Similarly, while mammographic images are discussed for implementation, it is to be understood that other medical images are also amenable to processing and display by the hardware and software system and method of the present invention.

Hardware

Figure 1:
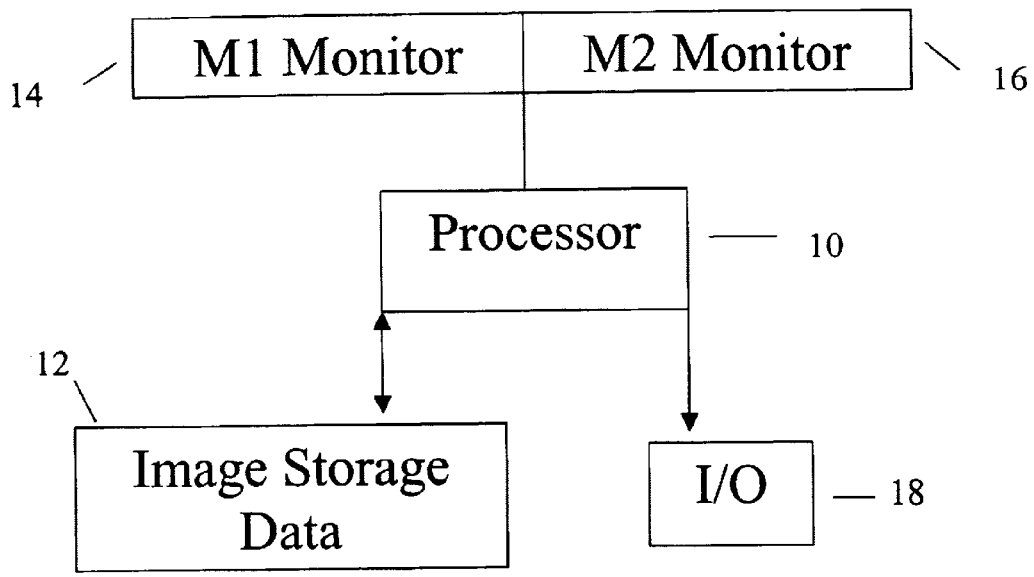
FIG. 1 is a schematic illustration of a system for use in implementing the principles of the present invention.
Figure 10:
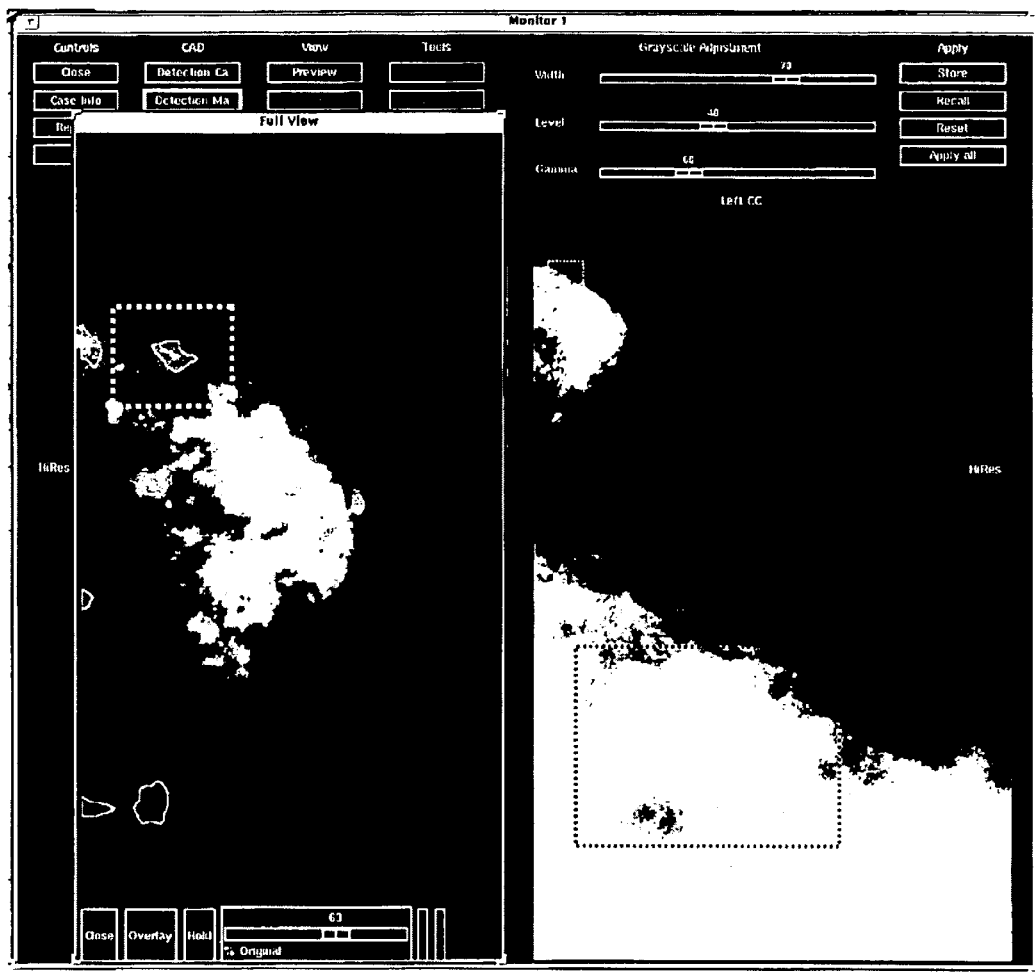

Until recently fast image processing, even on workstations, required the purchase of special-purpose imaging/graphics boards. The recent evolution of workstations, however, has changed this. Most major workstation vendors have now integrated fast imaging and graphics either in their central processing units (CPUs) or as support chips on the motherboard. Sun Microsystem's (Mountain View, Calif.) SX technology was one of the earliest integrated solutions, and the most powerful at the time of introduction.[9] The SX was an on-board chip that assisted the SPARC CPU in pixel processing. Along with Sun's X Imaging Library (XIL), which was optimized for the SX-based machines, real-time panning and zooming of large medical images was now possible on standard workstations. With the introduction of the UltraSPARC CPU, Sun has integrated the functionality of the SX technology into the CPU, thus making fast imaging possible in every workstation. The computer chosen by applicants to implement the present invention was the UltraSPARC 2200, a dual-processor 200-MHZ system (FIGS. 1, 10), with 512-MB RAM running under the Solaris 2.5.1 operating system. Table 1 shows the imaging performance numbers for 8-bit images obtained from Sun's Graphics Overview Brochure:

TABLE 1

Imaging Performance of the UltraSPARC 2200 Creator

| Imaging operation | Performance (MPixels/sec) |
|---|---|
| Fill | 603.2 |
| Pan/Copy | 156.2 |
| Convolve (3 × 3) | 24.2 |

While the pixel processing and display operations were sped up by the hardware, the standard disks based on the SCSI bus with a speed of 10 MB/sec were not fast enough to retrieve mammographic images on demand at high speeds. To alleviate this problem, and to facilitate a large database of high-resolution digital mammographic images, a Sun SPARCstorage Array with a capacity of 37.8 GB was included. Being based on a fiber channel architecture, disk-to-host transfer speeds of up to 25 MB/secwere now possible. A complement to the disk storage system is the Sun SPARCstorage Library 12, a 7-slot Digital Linear Tape (DLT) array that can act not only as a backup device but also, with the appropriate Hierarchical Storage Management (HSM) software, as a third-level storage for aging studies to tape.

Figure 2:
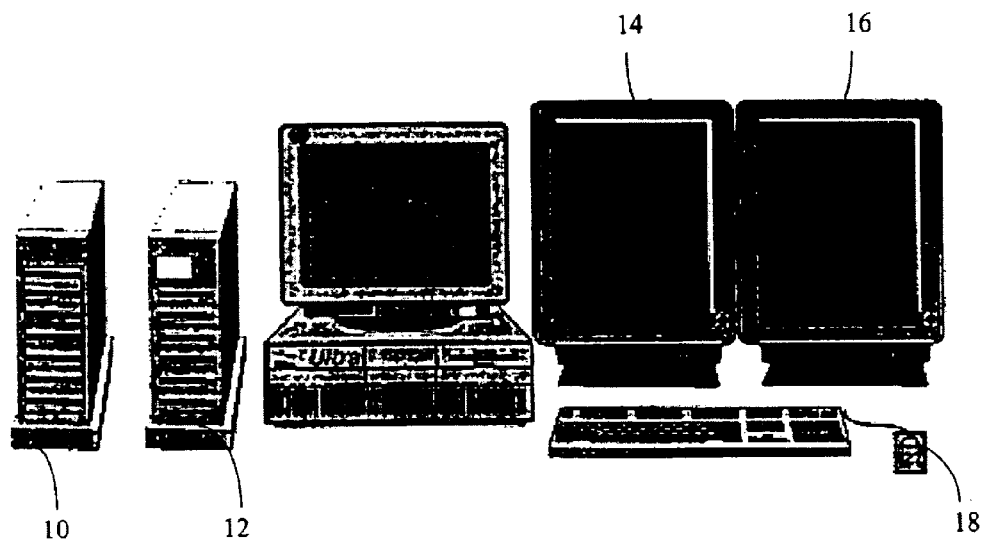
FIG. 2 is a front view of exemplary hardware components of the system.

The characteristics of display monitors 14,16 are important to proper implementation of the present invention. Screen film mammography is interpreted on viewboxes with an average luminance of about 3000 nit (880 ft-L),[10] which gives excellent back-lighting to x-ray films. In contrast, the typical color monitor provided with the Sun workstations is only about 30 ft-L. The maximum display resolution of 1280×1024 pixels with standard monitors is not enough for x-ray films digitized at 30 μm/pixel, which are in the range of 3000×5000 pixels. Dome Imaging Systems Inc. (Waltham, Mass.), manufactures 5-megapixel display cards for the Sun that are capable of driving high-resolution grayscale monitors. The monitors 14, 16 chosen are the DR-110 from Data Ray Corp (Westminister, Colo.). These are 2048×2560 pixels at 74 Hz, with a luminance of 120 ft-L and 30 transmissivity. A dual-monitor setup was selected (FIGS. 1 and 2) to accommodate simultaneous multiple image display.

Software

The software was written in ANSI C, using SPARCworks Visual C++ for the interface development, and the Motif toolkit. Sun's XIL was used as the imaging library. The XIL library was accelerated for both the UltraSPARC's Fast Frame Buffer (FFB) as well as Dome's MD5 boards. The Java language was used for the report recording software.

This combination of hardware and software provided a solid base for the display station project.

Image Data

The source of the mammographic images used in this embodiment of the present invention is the I magclear R3000 x-ray film digitizer by DBA Systems (Melbourne, Fla.). The digitizer is capable of scanning films at 30 μm/pixel and 16 bits/pixel. The standard x-ray films are 19.05 cm×22.86 cm, resulting in scanned images that are 6350×7620 pixels. Of this, the breast area covers a smaller region, and thus the images are cut to preserve only this area. After the trimming, the average mammographic image is about 3000×5000 pixels in size.

Design Choices and Implementation

The interface was designed to depict as closely as possible the standard mammography viewbox reading while including all the assets of a digital display in a most intuitive way. Such choices are believed to facilitate a clinician's making a smooth transition to the present system. Naturally the invention is not intended to be limited by such design choices for future developments.

The issues considered in the development of the interface fall into three major categories: (a) display layout and analysis tools, (b) speed of display and analysis, and (c) reporting tools. Each category is discussed in detail below.

Display Layout

Figure 3:
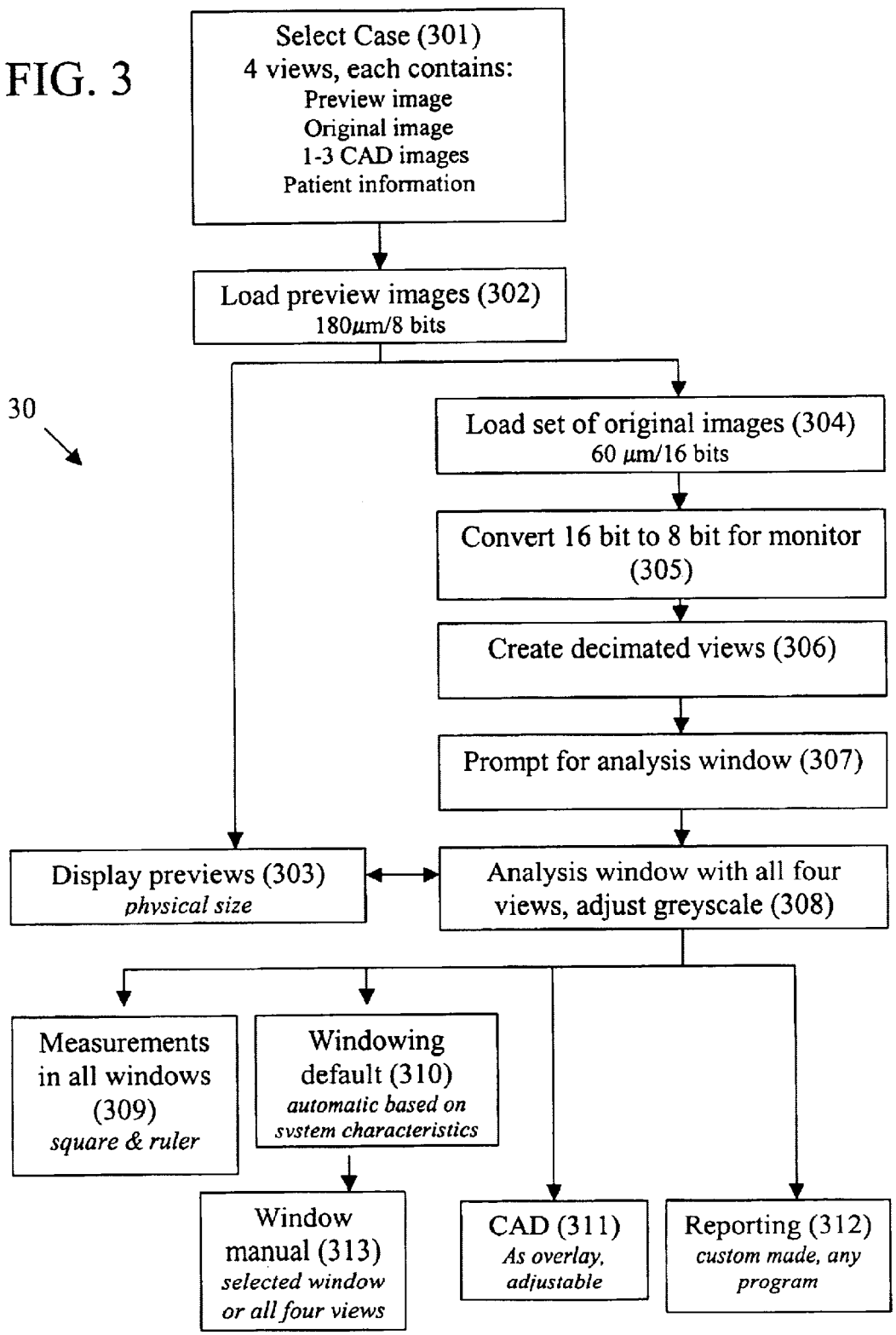
FIG. 3 is a flow chart showing the sequence of steps in implementing the workstation interface to display a case to a user.
Figure 13:
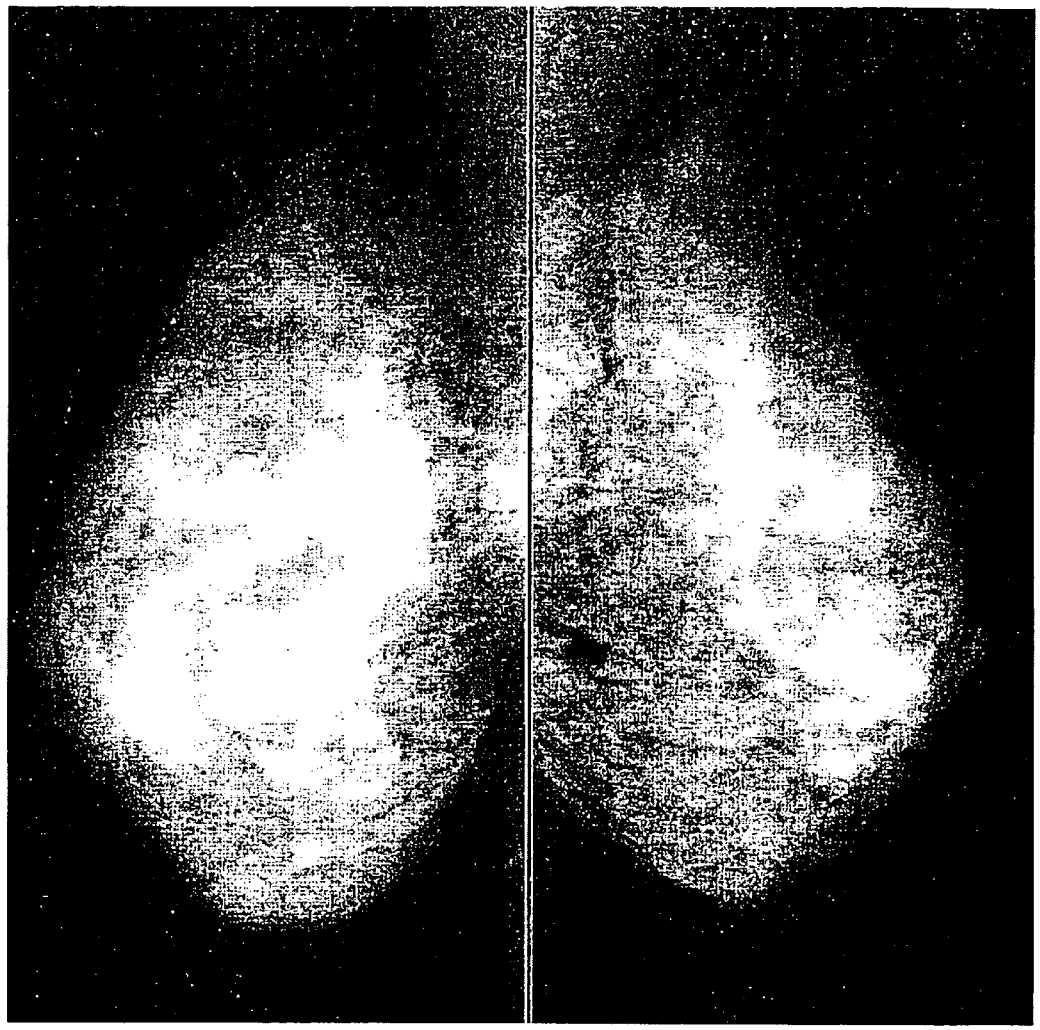

Images are presented and organized in a way based on reviews of current mammography reading practices of radiologists. A flow chart of a typical case analysis procedure 30 with the use of the present invention is presented in FIG. 3. At the beginning of every case evaluation, the radiologist is offered a case selection menu (block 301) from which the case to be read is selected. This is, as most of the other handling, done using a pointing device, for example, by pointing and clicking with a mouse 18, just as in with other software common in the art. Depending on the study, a case may contain single-view or standard four-view mammograms (left and right medio-lateral, ML; left and right cranio-caudal, CC). It may also contain processed versions of the originals by CAD techniques as well as text files with patient information. After a case is selected and the preview images loaded (block 302), an initial full-size overview (block 303) is presented, as shown in FIG. 3 [(FIG. 13)]. The CC views are displayed on one of the two monitors 14,16 of the workstation, the ML views on the other, in an arrangement similar to the current practice in screen/film mammography. This configuration is intended to provide the physician with a first global overview of the case. When ready, the observer can proceed to the analysis part of the interface, which replaces the global views by a window 40 shown in FIG. 4 (one per monitor; blocks 304,305), containing, e.g., left 41 and right 42 CC views. The radiologists are always able to go back to the global overview (button 401) and look at the case at a glance.

In the analysis window, decimated views 41,42 of the original images are provided in the upper section (block 306). In the lower part two windows 43,44 display selected sections (indicated by squares in the decimated views, block 307) at high resolution, i.e., from the original data. This arrangement enables the physician to keep the overview at anytime of the analysis while looking at the high-resolution sections (block 308).

For an easy and fast reading, panning as well as jumping to certain locations in the image is possible. This is done by using the mouse 18 as pointing or dragging device, as in other common software. Depending on the preferred reading style of the radiologist, panning can occur in either the decimated or the high-resolution windows. It turned out that a common practice is to scan through the image in the decimated view but pan in the high-resolution view for a thorough and slow examination of certain regions of interest.

One of the main features of the interface is the real-time grayscale adjustment (button 402, block 308). Three scales allow one to set, with controls shown on the top right corner of FIG. 4, for example, the window width (button 404) and the level (button 405) and to change the gamma value (button 406). Changes can be made in one of the smaller windows, which is transmitted to its respective selected section window (see FIG. 5, 51,52), and then applied to all four of the smaller windows on both monitors. Due to the nature of mammography and inherent nonuniformities, each image may also be individually adjusted. For quick settings, preferred values may be stored and applied to as many different images as desired.

Figure 6:
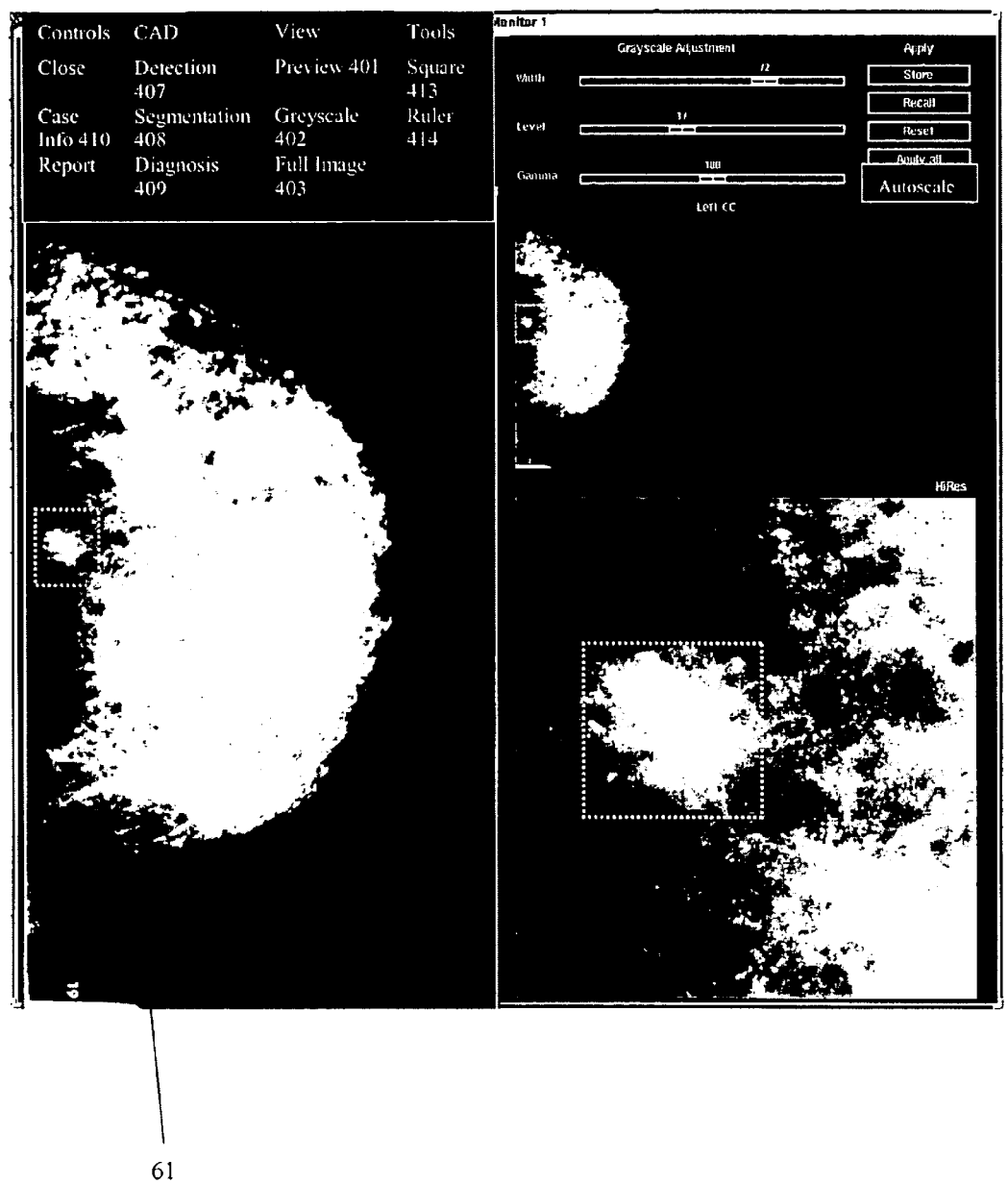

A full ("popup") image may also be viewed (FIG. 6, 61) by selecting button 403 on the control panel.

Further, automatic scaling may be imposed in order to optimize the appearance and visual interpretation of the images from monitors. Selecting the "autoscale" button 411 activates a scaling process based upon a model that takes into consideration the properties of the film and the digitizer, the monitors, and human vision and then matches them for optimal reading. The scaling is typically different for each set of images, and selecting this button 411 applies the same scaling function to all images in the set (e.g., the four mammogram views). Manual interactive adjustment is, of course, also available.

In addition to these primary images, the interface allows the display of CAD results if desired with the use of a real-time classification feature (block 311). The radiologist can select a suspicious area on the screen and obtain a computer analysis and diagnosis using CAD results in the form of segmentation and/or detection of an abnormality, such as calcifications or masses, image enhancement, and/or diagnosis, i.e., computer classification of an identified abnormality as benign or malignant. All these methods have been developed in our laboratory.[11] These CAD images are displayed upon selection of the appropriate button from the controls in any of the windows, which are linked to the originals so that panning or clicking in a certain region of interest also alters the views in the decimated and high-resolution windows. For easier orientation, the reader can also bring up a full view of either the right or left image and pan in the same way as in the images previously described.

Selection of the "detection" button 407 causes the system to display a combined detection image including the outputs of one or more computer programs that are designed to detect different abnormalities (e.g., masses, calcifications, architectural distortion).

Figure 9:
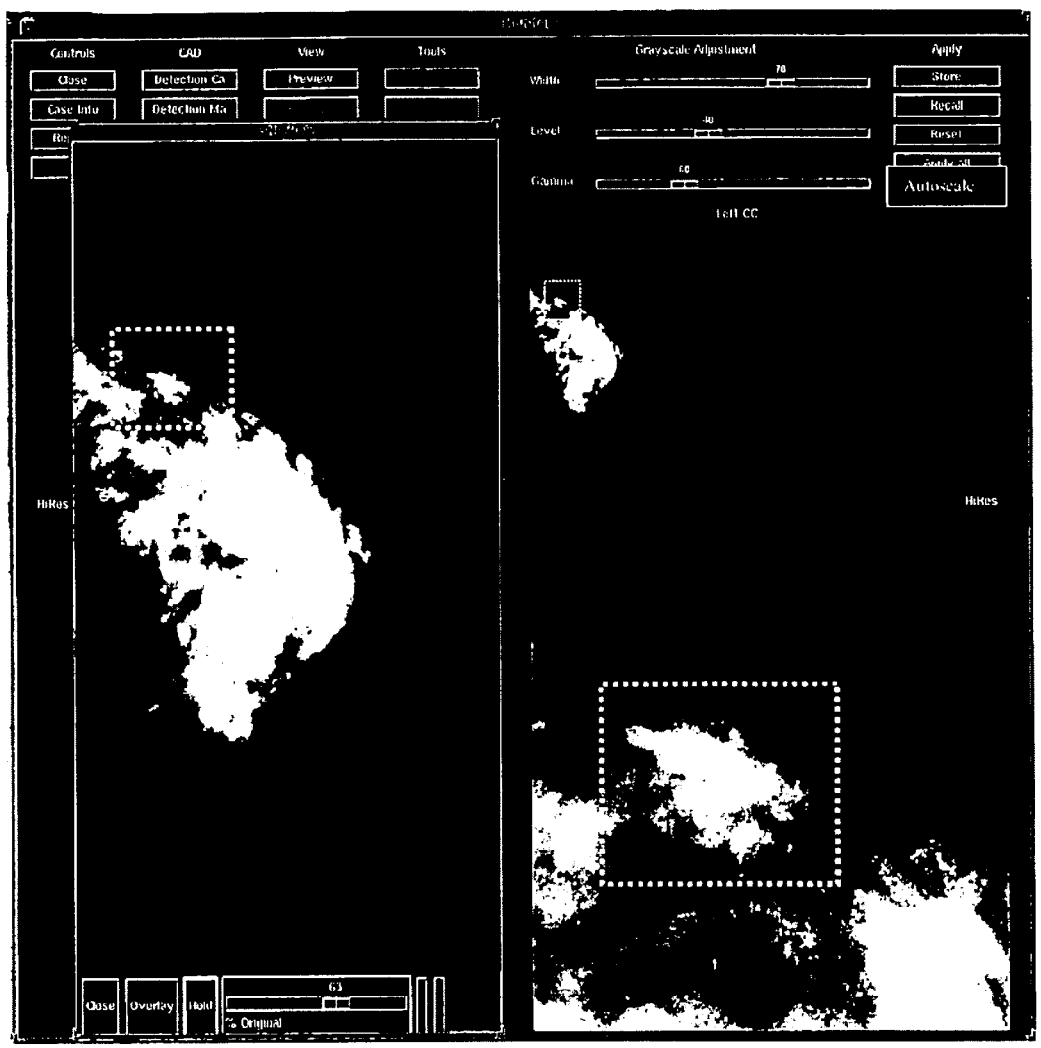

Selection of the "segmentation" button 408 permits the viewing of a finding from a specific small region of the image with an outline of any found mass. This is done is real time with an image segmentation algorithm within the interface software. A popup window displays the output of the computer segmentation process. It is also possible to permit the radiologist to manually (e.g., with the mouse 18) outline a suspicious region and then proceed with automated diagnosis, or to outline a section of breast parenchyma to obtain an automated estimate of the density. See FIGS. 9 and 10 for representational images before and after overlaying a CAD image thereon.

Selection of the "diagnosis" button 409 accesses a computer-determined likelihood of malignancy in a specified region. The radiologist in a particular embodiment selects a region of interest by clicking with the mouse 18 at the center of the region, as for the segmentation process. The region is processed in real time with segmentation and classification algorithms. The outline of the finding is presented to the radiologist in a popup window. The probability of the finding to be malignant estimated during the classification process is displayed in another window.

Figure 11:

Patient information is available through the whole process of analysis and can be shown or hidden at any time by selecting the corresponding button 410 in the controls (FIG. 11).

Figure 4:
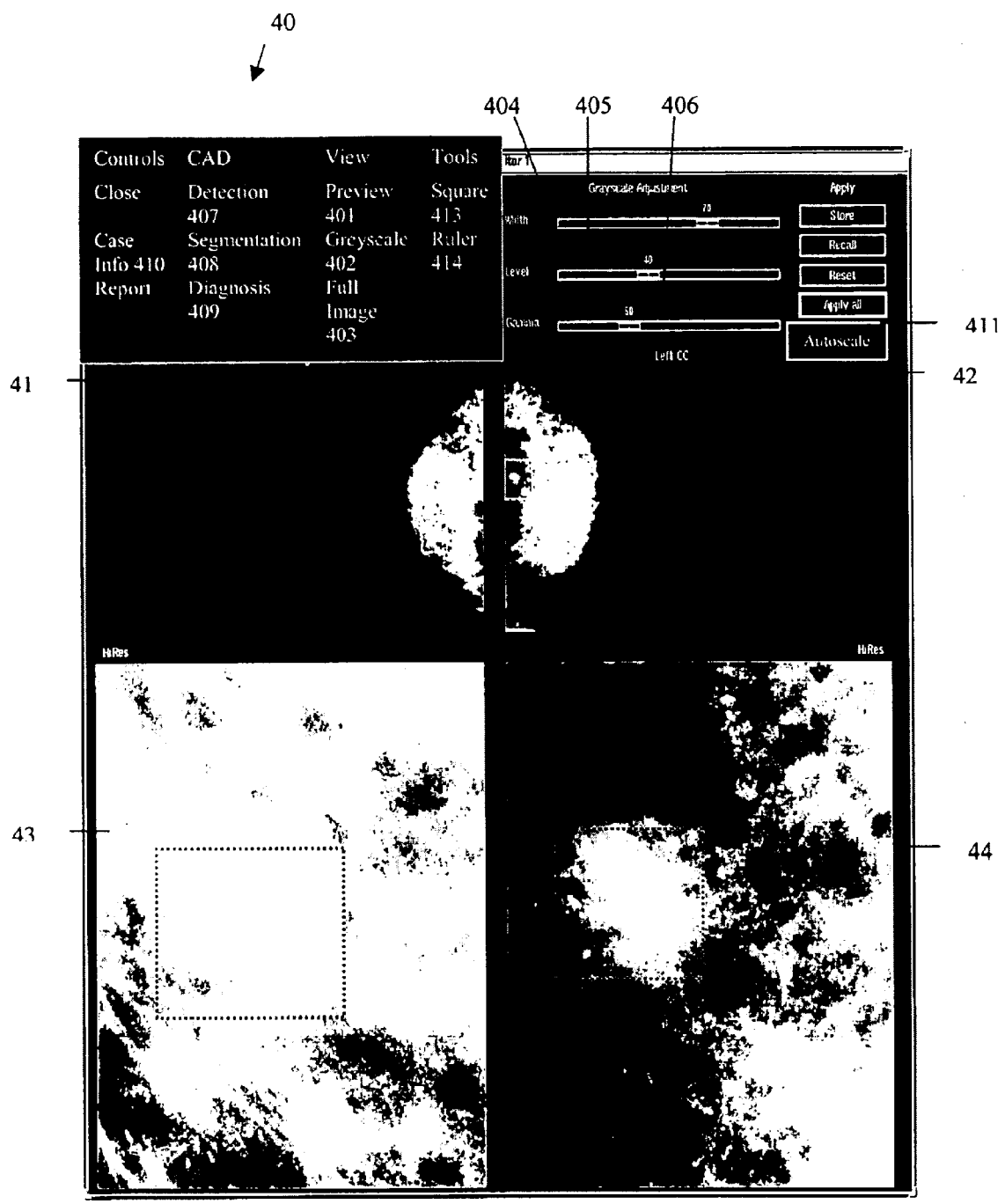
Figure 5:
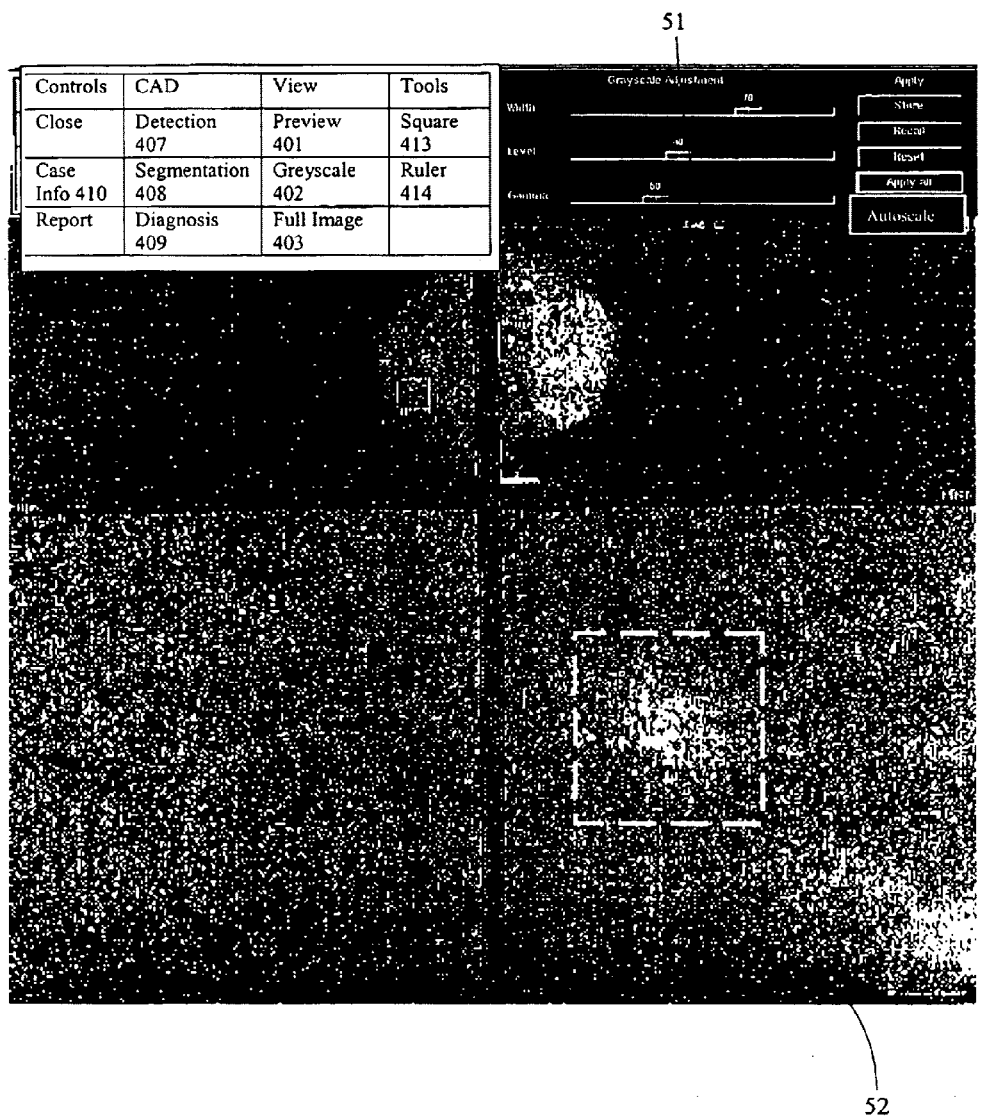
Figure 7:
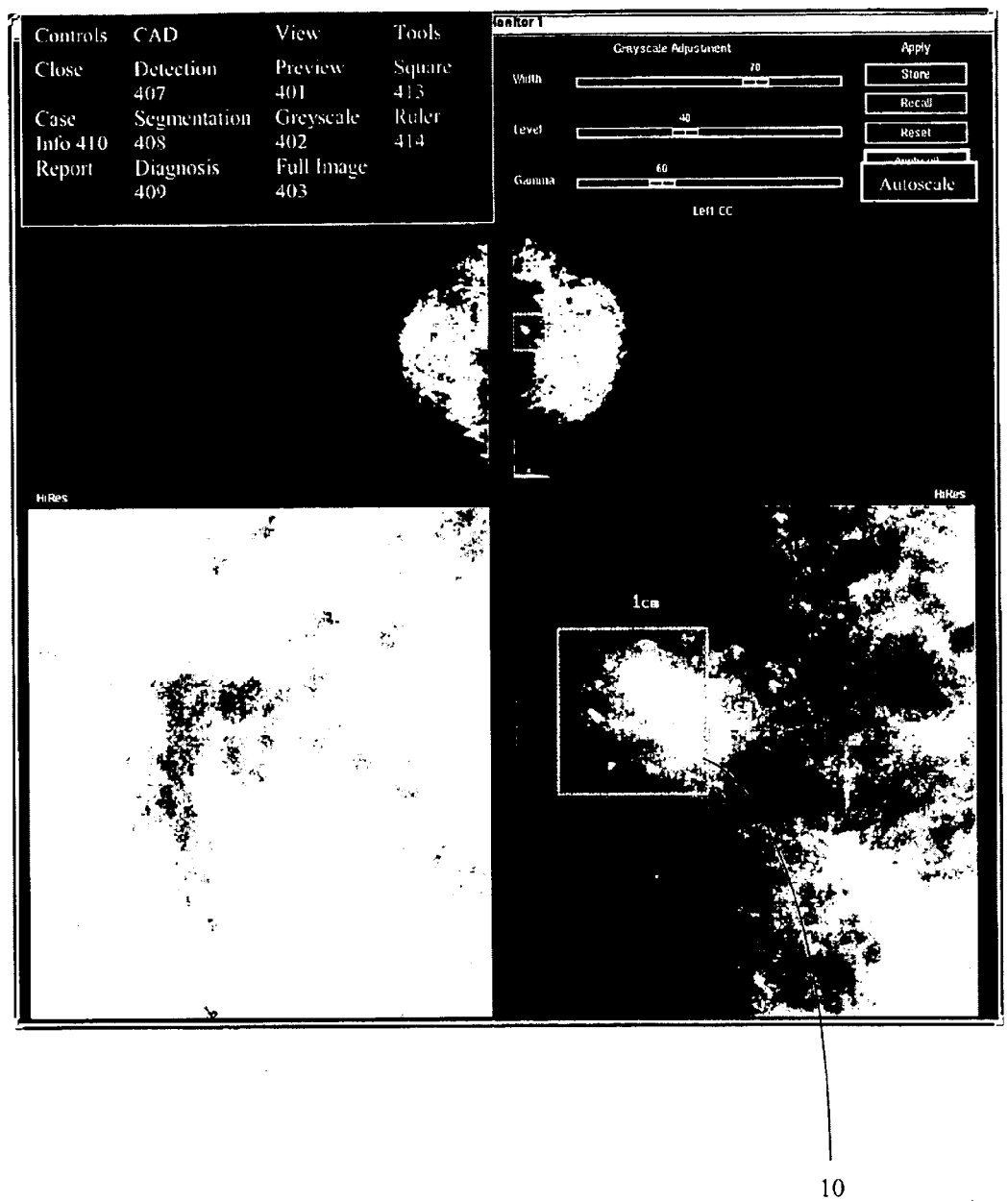
Figure 8:
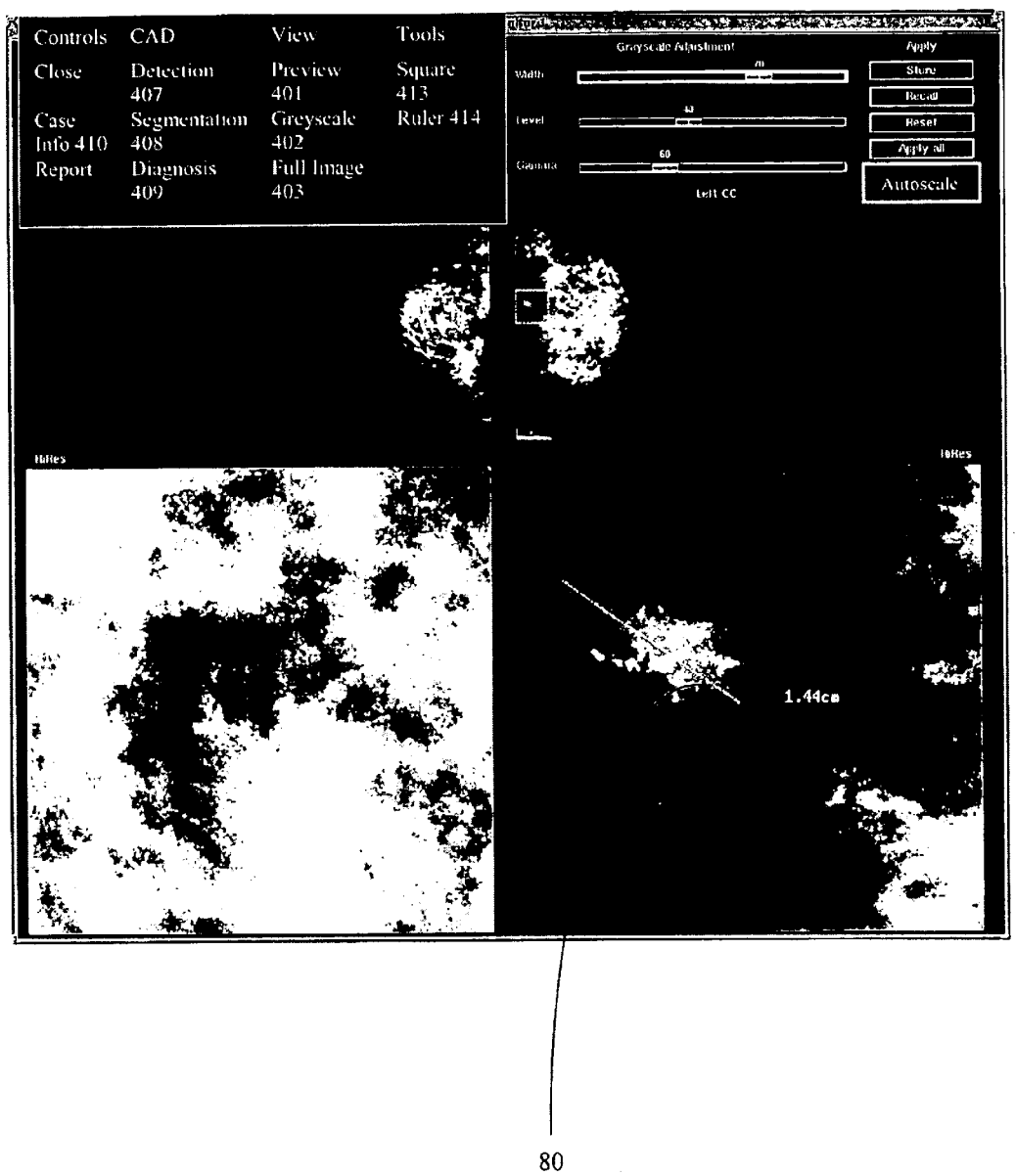

Finally, mammography evaluation requires the need of measuring dimensions (block 309). In the current implementation, the radiologist is able to display and move around a 1 cm box 46 in any image of any resolution (FIG. 4). Tools that will provide measurements of the dimensions of a suspicious region include a measuring square 70 (FIG. 7) and a measuring ruler 80 (FIG. 8), accessed by selecting the appropriate buttons 413,414 on the controls.

Speed

A significant issue in the development of the interface was the speed with which images are displayed and analysis is done. To be an acknowledged alternative to traditional mammogram reading and to avoid biases, the speed of the interface has to be comparable to the speed of film reading. The hardware and software used here are sufficient enough to enable quick display, panning, and grayscale adjustments. Most operations are done in real time (see Tables 1 and 2). Slightly slower is the display of the interface itself, which is due to the speed of the Motif-library function calls and the general speed of the server and client transactions. A problem faced while developing the interface is that it takes a relatively long time to load and prepare the images. The idea to avoid the loading delay by multithreading (MT) the process failed due to the lack of MT-safeness of X-Windows, Motif, and XIL. A practical solution to this problem was to load all primary images at the very beginning, while the radiologist is looking at the global view, and keep them in memory. The overview images are lower-resolution, reduced-size images and are displayed in a short time period (Table 2). By the time the reader proceeds to the analysis, all images are generally loaded. The CAD images are loaded on demand and are also kept in memory for quick further access. A disadvantage to this approach is that no action is possible while the overview is presented and the images are being loaded.

TABLE 2

Average time for interface operations

| Interface operation | Time (sec) |
| --- | --- |
| Load four overview images from disk | 1 |
| Load four high-resolution images from disk | 8 |
| Change contrast/brightness level of all 4 images | 0.5 |
| Display full views | 1.5 |
| Load and display enhanced image | 1 |

Report

When the reading of the case is completed, the radiologist can record the diagnosis by selecting the "Report" option 412 from the case selection window. An online form is then displayed (FIG. 12) where the observer inputs the following information: (a) interpretation category using the Breast Imaging Reporting and Data System of the American College of Radiology, (b) finding, (c) location, (d)followup recommendation (if applicable), and (e) breast composition (parenchymal density category).

The reporting format is designed to be easily changed to accommodate the needs of a particular study. The report is saved in a file that serves as input to the ROC analysis stage.[12–14]

Conclusions

Applicants had set out to develop a workstation-user interface that can be used in studies of CAD methods for digital mammography. Such objectives were successfully realized, including the implementation of the foregoing interface, which is:

usable in a clinical environment for primary mammography reading easy to use functional real-time responsive flexible and extensible in design Applicants found that with this design these requirements were satisfied, not only for this study, but for possible future clinical and educational uses in mammography and other medical imaging modalities.

The software was written using standard tools in the Sun-based UNIX environment, thus providing an excellent product that runs even on an entry-level SPARCstation 4 without any additional hardware. Enhanced with high-resolution display boards and grayscale monitors, the applicability extends to clinical usage. A Microsoft Windows NT port of Sun's XIL has been in the works, which will mean easy portability to the PC platform, thus reducing costs even further. These devices and platforms are exemplary and are not intended as limitations of the invention.

While the current disclosure comprises a software-based implementation, alternative electronically implementable means are also contemplated, such as a VLSI architecture for compressing and decompressing images. An example of such technology comprises a patent issued to Ranganathan et al. (U.S. Pat. No. 5,659,362), the disclosure of which is incorporated herein by reference.

REFERENCES

1. S. Dwyer III and B. Stewart, "Clinical uses of grayscaleworkstations," in Proc. of AAPM Summer School, pp. 243–66 (Charlottesville, Va.), Aug. 1993.
2. S. Dwyer III, M. Williams, and L. Fajardo, "Full breast digital mammography and PACS requirements," in Proc. Third International Workshop on Digital Mammography, p. 19 (Chicago, Ill.), June 1996.
3. A. Giles, A. Cowen, and G. Parkin, "A clinical workstation for digital mammography," in SPIE, vol. 1905, pp. 806–17, 1993.
4. P. Fisher, P. Mutalik, I. Maddison, et al., "Mammo/Icon: Voice activated intelligent radiologic image display," in SCAR computer applications to assist radiology, R. L. Arenson and R. M. Friedenberg, Eds., pp. 713–19, Symposia Foundation, Anaheim, Calif., 1990.
5. M. L. Giger, "Computer aided diagnosis." RSNA Categorical Course in Physics, pp. 257–74, 1993.
6. C. Metz, "Some practical issues of experimental design and data in radiological ROC studies," Invest. Radiol. 24, pp. 234–45, 1989.
7. G. Cox, A. Templeton, and S. Dwyer III, "Digital image management: Networking, display and archiving," Radiologic Clinics of N. America 24(1), pp. 37–54, 1986.
8. S. Parker, J. Lovin, W. Jobe, J. Luethke, K. Hopper, W. Yakes, and B. Burke, "Stereotactic breast biopsy with a biopsy gun," Radiology 176(3), pp. 741–47, 1990.
9. W. Donovan, P. Sabella, I. Kabir, and M. M. Hsieh, "Pixel processing in a memory controller," IEEE Computer Graphics and Applications 15(1), pp. 51–61, 1995.
10. A. Haus, J. Gray, and T. Daly, "Evaluation of mammographic viewbox luminance, illuminance, and color," Med. Phys. 20(3), pp. 819–21, 1993.
11. W. Qian, L. P. Clarke, B. Zheng, M. Kallergi, and R. A. Clark, "Computer aided diagnosis for digital mammography," IEEE Eng. Med. Biol. Mag. 14(5), pp. 561–69, 1995.
12. C. Metz, "Quantification of failure to demonstrate statistical significance: The usefulness of confidence intervals," Invest. Radiol. 28, pp. 59–63, 1993.
13. C. Metz, "ROC methodology in radiologic imaging," Invest. Radiol. 21, pp. 720–33, 1986.
14. D. Dorfman and K. Berbaum, "Degeneracy and discrete receiver operating characteristic rating data," Acad. Radiol 2, pp. 907–15, 1995.

What is claimed is:

1. A system for providing an interface between a digitized mammogram and a user comprising:
a processor having means for electronically communicating with:
means for communicating with a user;
a monitor for displaying image data in a predetermined format and in varying greyscale, the monitor having a predetermined illumination capability; and
means for receiving digitized mammogram data corresponding to a film mammogram image, the digitized mammogram data having greyscale values corresponding to optical densities of the film mammogram image; and
electronically implementable means resident in the processor comprising:

means for transforming the digitized mammogram data into a plurality of varying-resolution forms, each form having different greyscale values;

means for communicating with a monitor to display the plurality of forms, each form within a different window on the monitor, and each form having a predetermined illumination state corresponding to the greyscale values thereof; and means for receiving from the user communication means a control instruction for changing an illumination state in a displayed form and for implementing the control instruction upon the displayed form, thereby permitting the user to control the illumination state of each displayed form.

2. A system for interfacing a digitized mammogram to a user comprising:

a. a monitor capable of displaying image data in a predetermined format, and in varying grayscale colors, said monitor having a predetermined illumination capability;

b. an electronic storage medium with digitized mammogram image data, said digitized mammogram image data corresponding to a film mammogram image and the digitized mammogram image data having grayscale values corresponding to the optical densities of the film mammogram image;

c. a processor in circuit communication with said monitor and said electronic storage medium; and d. an input device in circuit communication with said processor;

said processor being adapted to receive input signals from said input device, and being responsive to a signal from said input device to transfer digitized image data from said electronic storage medium to said monitor in a way that causes the monitor to produce a display having a plurality of windows and to display a mammogram image in a different form in each window with grayscale values that, along with the illumination characteristics of said monitor, appears to a user as a mammogram in each window under a predetermined illumination state, thereby interfacing said mammogram image in each window and in a predetermined illumination state to an operator handling said input device;

said processor being adapted to receive further input from said input device related to the mammogram image in a selected window, said further input from said input device including input that selectively controls the grayscale values of the mammogram image in the selected window, thereby enabling an operator handling said input device to selectively control the illumination state with which the mammogram image in the selected window is displayed to the operator.

3. A system for providing an interface between a medical image and a user comprising:

means for establishing electronic communications with a processor for receiving a stored digitized medical image comprising data representative of a plurality of greyscale values;

means for communicating with a display means; and software means loadable into the processor comprising:
means for receiving a signal from a user-operable device;
means controllable by a signal from the user-operable device for transforming the image into a plurality of varying-resolution forms, each form having a different set of greyscale values; and
means for displaying the forms on the display means, each form displayed within a different sector of the display means.

4. The system recited in claim 3, wherein the display means comprises a first and a second display monitor.

5. The system recited in claim 4, wherein the first and the second display monitors each comprise a high-resolution greyscale monitor.

6. The system recited in claim 3, wherein the medical image comprises a mammographic image.

7. The system recited in claim 3, wherein the displaying means comprises means for selecting a display form from a plurality of display configurations.

8. The system recited in claim 7, wherein the selecting means comprises means for generating a menu of display configurations for displaying on the display means.

9. The system recited in claim 3, wherein the software means further comprises means for generating a zoom window overlayable on at least one of the displayed forms for identifying a portion of the form desired to be displayed as a magnified view in a different sector.

10. The system recited in claim 9, wherein the zoom window generating means is under signal control of the user-operable control device.

11. The system recited in claim 3, wherein the software means further comprises means for generating a measuring device overlayable on at least one of the displayed forms for measuring a feature thereof.

12. The system recited in claim 3, wherein the software means further comprises means for generating a panning of at least one of the displayed forms.

13. The system recited in claim 1, wherein the image transforming means comprises means for adjusting the greyscale values essentially in real time.

14. The system recited in claim 13, wherein the greyscale adjusting means comprises means for adjusting the greyscale values of all the displayed forms.

15. The system recited in claim 1, further comprising means for accessing with a computer-aided diagnosis system and for transmitting the image thereto for processing thereby, and wherein the displaying means comprises means for displaying the processed image.

16. The system recited in claim 3, wherein the software means further comprising means interactive with the user for generating a report containing diagnosis information.

17. A system for analyzing a set of digitized mammography images, the set comprising a plurality of views from a unitary patient, the system comprising:

a first and a second display monitor;

a processor having means for communicating with an image storage device and software means resident thereon, the software means comprising:
means for receiving a signal from a user-operable device;
means controllable by a signal from the user-operable device for transforming the image into a plurality of varying-resolution forms, each form having a different set of greyscale values; and
means for displaying a first form on the first monitor and a second form on the second monitor.

* * * * *